United States Patent

Haurilesko

[11] Patent Number: 5,544,621
[45] Date of Patent: Aug. 13, 1996

[54] METHOD AND DEVICE FOR FEEDING LIVE INSECTS TO FISH

[76] Inventor: Paul Haurilesko, 524 Sandra Dr., Level Green, Trafford, Pa. 15085

[21] Appl. No.: 354,645

[22] Filed: Dec. 13, 1994

[51] Int. Cl.⁶ ................................................ A01K 61/02
[52] U.S. Cl. ........................................................ 119/230
[58] Field of Search ................................. 119/200, 212, 119/230, 242, 51.01, 51.04, 6.6, 6.8, 6.5; 426/2

[56] References Cited

U.S. PATENT DOCUMENTS

| | | | |
|---|---|---|---|
| 2,539,633 | 1/1951 | Morrill | 119/6.5 |
| 4,002,146 | 1/1977 | Neff | |
| 4,019,459 | 4/1977 | Neff | 119/51.04 X |
| 4,036,189 | 7/1977 | Neff | 119/51.04 |
| 4,328,636 | 5/1982 | Johnson | |
| 5,150,666 | 9/1992 | Momont et al. | 119/51.04 X |
| 5,199,381 | 4/1993 | Masopust | 119/51.04 |
| 5,259,533 | 11/1993 | Kornfein et al. | 119/51.04 X |

Primary Examiner—Gene Mancene
Assistant Examiner—Thomas Price
Attorney, Agent, or Firm—Arnold B. Silverman; Eckert Seamans Cherin & Mellott

[57] ABSTRACT

A live insect feeder for use with a tank, such as an aquarium or a terrarium containing a live fish or animal that feeds on the live insects, includes a container having an opening through which an adult flightless insect can pass, and a tacky substance encircling the opening on the outside of the container. A medium for feeding the insects is contained within the container. When fertile eggs of the flightless insect are introduced into the container, the larvae that hatch from the eggs feed upon the food medium until they reach the adult stage. They either remain within the container, breeding a new generation of insects, or pass through the opening. When the container is positioned with the opening over the tank, the flightless insects passing through the opening either fall off or jump off into the tank thereby becoming food for the fish or animal living within the tank.

17 Claims, 2 Drawing Sheets

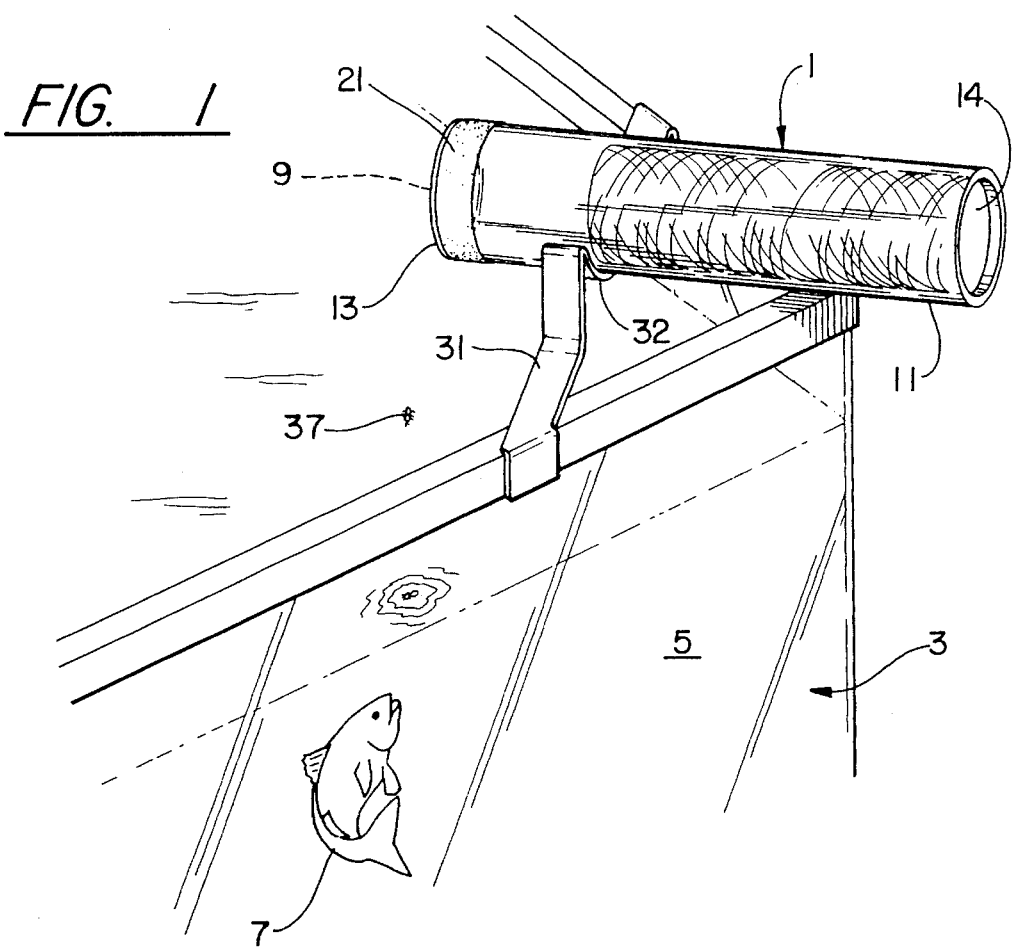
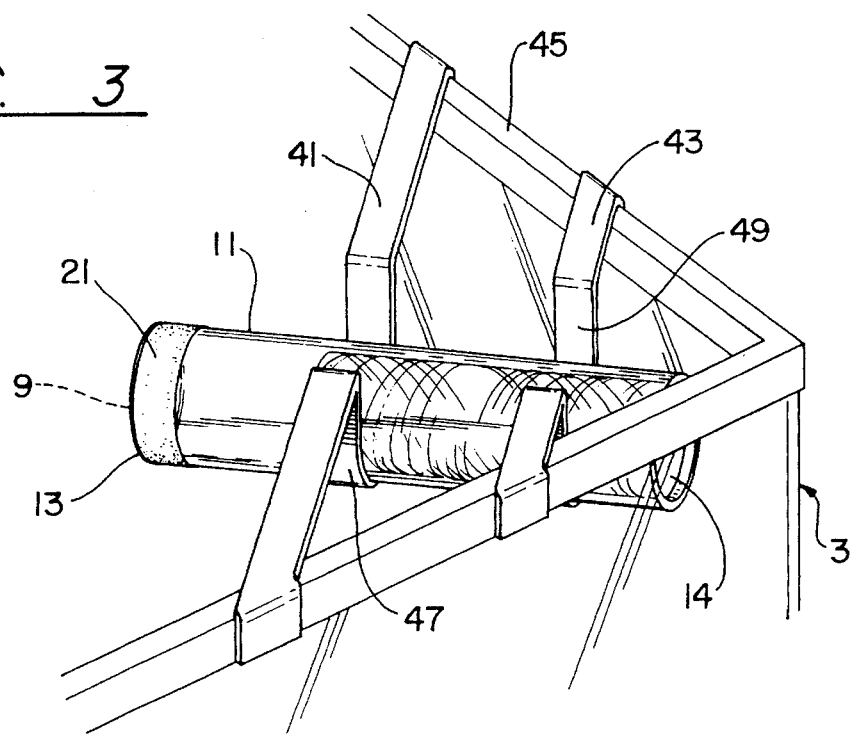

5,544,621

METHOD AND DEVICE FOR FEEDING LIVE INSECTS TO FISH

BACKGROUND OF THE INVENTION

1. Field of the Invention

The invention relates to live insect feeders, and, in particular, to devices and methods for rearing captive insects and introducing the insects into aquariums or terrariums.

2. Description of the Prior Art

Live insects are an excellent food for fish living in aquariums and for small animals, such as, for example, reptiles and amphibians, living in terrariums. Pet owners may purchase supplies of live insects for feeding their fish or other animals. However, some people may not want to handle the live insects, and, if the pet owner leaves home for a period of days, arrangements must be made to have someone else come into the home to feed the insects to the pets.

U.S. Pat. No. 4,328,636 discloses an insect control device which may also be used as a fish feeder. The device includes a cup-shaped container into which a bait may be placed. The container includes a plurality of small openings in its walls. Insects from outside the container are attracted to the container by the bait. The insects lay their eggs through or near the openings in the container wall. When the eggs outside the container hatch, the tiny larvae are attracted to the inside of the container by the bait. However, the openings are too small to permit larger insect larvae and adult insects to pass. Once inside the container, the larvae feed on the bait and grow. In a short time the insect larvae are too large to escape the container. When the device is used for feeding fish, the feeder is mounted on a floating platform above the water of an aquarium. The container is positioned above the water and another enclosed space is defined below the container. A partition between the container and the second enclosed opening has a plurality of openings which permit the adult insects to pass therethrough. The adult insects, eggs and larvae may fall from the second enclosed space through the platform and into the water where they may be consumed by fish in the water.

U.S. Pat. No. 4,002,146 discloses an apparatus for collecting insects and feeding the insects to fish contained in a floating cage. A cover over the cage includes a funnel-shaped opening. An ultraviolet lamp is positioned in the lower portion of the funnel-shaped opening. When the light is illuminated, it is visible to insects flying above the funnel, but not to those at or below the level of the funnel. An electric fan positioned below the ultraviolet lamp creates a downward flow of air within the funnel. Insects flying above the funnel are attracted to the light from the lamp and fly toward it. Once inside the funnel the downward momentum of the insects and the downward airflow created by the fan cause the insect to continue downward through the funnel and into the open space between the water and the top of the enclosure, where they are trapped. Downward air pressure caused by the fan prevents the insects from escaping. The insects eventually fall to the water and are consumed by the fish living in the cage.

U.S. Pat. No. 4,019,459 discloses an animal enclosure which includes an insect collection apparatus similar to that disclosed in U.S. Pat. No. 4,002,146. The device may be used to feed aquatic animal cultures or amphibious animal cultures.

U.S. Pat. No. 4,036,189 discloses an apparatus for attracting water-borne insects into a submerged enclosure. The apparatus includes an ultraviolet lamp positioned above the enclosure and shining down into the water. The illumination caused by the lamp attracts water-borne insects which may be consumed by the fish living in the enclosure.

All of the prior art live insect feeders rely upon attracting adult insects from the environment around the fish tank or a terrarium to be either fed directly to the fish or animals or to breed a new generation of insects to be fed to the fish and animals. It is generally not desirable to invite live feral adult insects into a home or business in an uncontrolled fashion on the chance possibility that they will become food for an animal living in an aquarium or terrarium. Feral insects can carry dirt and disease causing microbes. Therefore, there is a need for an improved live insect feeder that does not rely upon preexisting vermin in the home.

SUMMARY OF THE INVENTION

These objects and others are obtained with the present invention for a live insect feeder that includes a container with an opening, a medium for feeding insects disposed within the container, a tacky substance located on the outside of the container adjacent the opening and surrounding the opening of the container, and a mechanism for attaching the container to a wall of a tank, such as, for example, an aquarium or terrarium such that the opening of the container can be positioned above fish or animals living therein.

Viable eggs of a species of flightless insect are introduced into the medium, either directly or by introducing adult or larval members of that species to breed and lay their eggs in the medium. When the eggs hatch, the larvae feed on the medium and metamorphose to an adult stage. The adults, and some larvae, move to the edge of the container at the opening. The container is preferably a tube oriented about horizontally. The insects either fall off or jump off into the tank, where they can be thereafter consumed by the fish or animals living in the tank. The tacky substance around the perimeter of the opening resists the insects crawling off around the outside of the container and escaping and inhibits entry of feral insects. Some of the adult insects will stay within the container and breed a new generation of insects which can thereafter become food for the animals in the tank. This process can continue for several generations until the insect feeding medium is exhausted, thereby producing a continuous supply of live insect food for weeks or even months It is an object of the present invention to provide a live insect feeding system for aquariums and terrariums.

It is another object of the invention to provide a live insect feeder that does not rely upon attracting adult feral insects from the vicinity of the feeder.

It is another object of the invention to provide a live insect feeder that will provide a substantially continuous supply of live insects for several weeks.

It is another object of the invention to provide a live insect feeder that is inexpensive and easy to use.

It is another object of the invention to provide a live insect feeder that will not introduce insect-borne diseases into the area in which the feeder is used.

It is another object of the invention to provide a live insect feeder that does not require electricity and does not have moving parts.

These and other objects of the invention will be more fully understood from the following description of the invention with reference to the illustrations appended hereto.

BRIEF DESCRIPTION OF THE DRAWINGS

FIG. 1 is a perspective view of a preferred embodiment of a live insect feeder of the invention positioned over an aquarium containing fish.

FIG. 3 is a perspective view of the invention showing a different support mechanism than that illustrated in FIG. 1.

DESCRIPTION OF THE PREFERRED EMBODIMENTS

Figure 2:
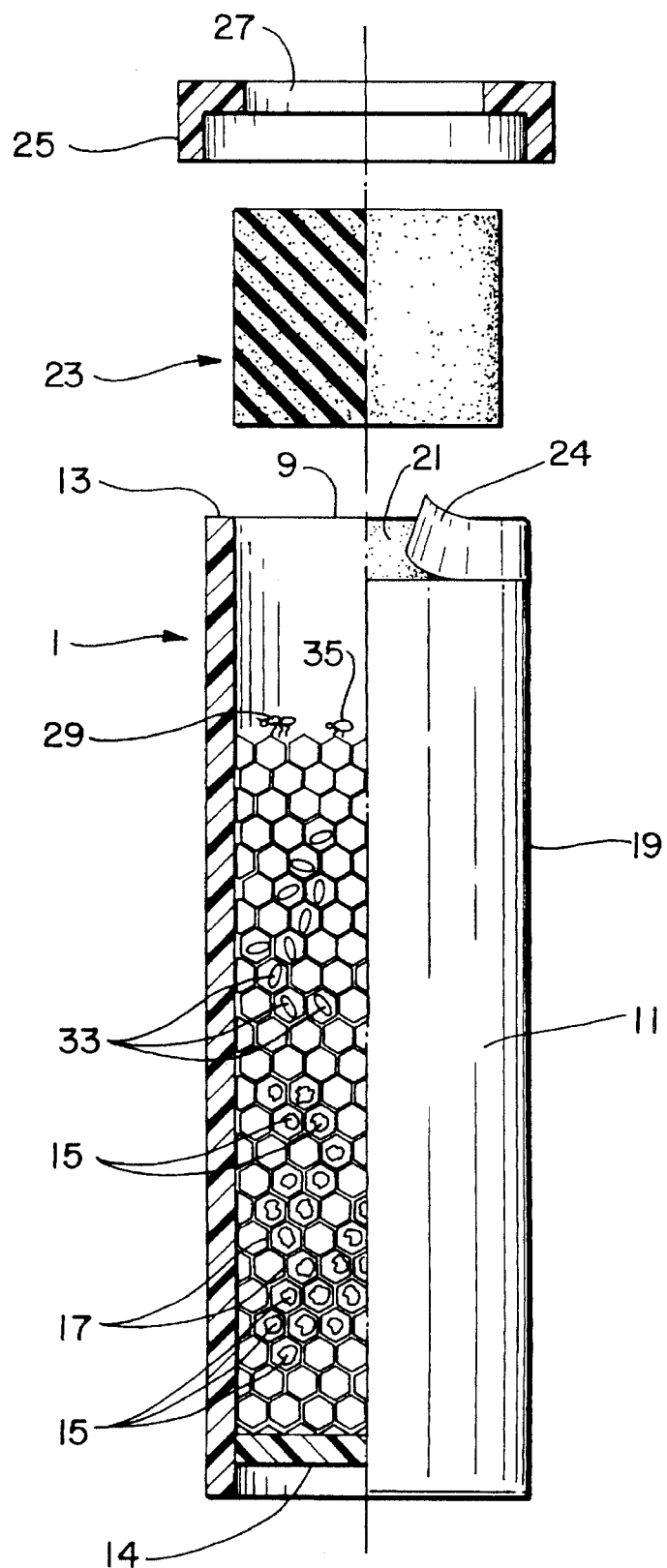
FIG. 2 is an exploded view and partial cross-section of an embodiment of the invention.

Referring now to FIG. 1, a live insect feeder 1 of the present invention is shown in use with a tank 3 containing water 5 and live fish 7. In FIG. 2, the live insect feeder 1 includes a container which is preferably a plastic tube 11 having an opening 9 at an open end 13, closed at its other end 14 and containing an insect feeding medium 15 supported and held in place within the container 11 by a support structure, such as, for example, plastic screening 17. On the outer surface 19 of the tube 11 and about adjacent the open end 13 there is a strip of a tacky material 21 that surrounds the opening. The tacky material 21 can be a piece of double-sided sticky tape, or some other suitable adhesive material such as, for example, that used for fly paper.

It is preferred that the live insect feeder be packaged initially with a plug 23, which is preferably fabricated of a porous, soft material, such as sponge rubber, a removable covering 24 for the tacky material 21, such as, for example, waxed paper, and a cap 25 that includes an opening 27 for permitting air to enter the tube 11 with the plug 23 in place. The plug 23 and cap 25 inhibit stray feral insects from entering the tube 11 before being positioned over a tank 3. The plug 25 permits some air to enter the tube 11 while maintaining a humidity level therein conducive to breeding insects. The tube 11, along with the insect feeding medium 15 and the screening 17, are preferably a Drosophila Culture Vial, which can be obtained from Carolina Biological Supply Company, of Burlington, N.C. The tacky material 21 and covering 24 are not included and must be applied to the vial. The plug 23 can be a Drosophila Culture Vial Plug, and the cap 25 can be a Drosophila Culture Vial Cap, each obtainable from Carolina Biological Supply. The Drosophila Culture Vial can be obtained from Carolina Biological Supply with fertile adult drosophila flies 29 of a flightless variety. This is a fast breeding type of insect that reaches an adult stage from an egg in only a few days. Alternatively, the tube 11 can be loaded initially with fertile eggs 33 or larvae 35 of the flightless drosophila flies or of another flightless insect species.

The adult insects 29, illustrated in FIG. 2, will lay eggs 33 on the insect feeding medium 15 within the tube 11. The eggs 33 will soon hatch, and the larvae 3B will feed on the insect feeding medium 15 until they reach the adult stage.

When it is observed that there are sufficient adult insects 29 within the tube 11 to begin feeding, the cap 25 and plug 23 are removed from the tube 11 and the covering 24 removed from the tacky material 21. The tube 11 is then placed over an open tank 3, such as, for example, an aquarium or terrarium, containing fish or animals that eat live insects, such that the open end 13 extends over the inside of the tank 3, as illustrated in FIG. 1. A support structure, such as, for example, a substantially flat rod 31 positioned over a corner of the tank 3 can be used to balance the live insect feeder 1 in an about horizontal position over the tank 3. The rod 31 preferably includes an indentation 32 to inhibit the tube 11 from rolling out of position.

The new generation of adult insects 37 will either remain within the tube 11 to breed and produce more eggs 33 or will crawl to the open end 13. The flightless insects 37 at the open end 13, not knowing that they cannot fly, will jump off the end of the tube 11 through the opening 9 or simply walk off or fall off the open end 13 into the tank 3, thereby becoming food for fish 7 or other animals within the tank 3. Those insects that attempt to crawl around the lip at the open end 13 will encounter the tacky material 21, get stuck or retreat, and not escape. The tacky material 21 also serves to inhibit entry of feral insects into the container.

Referring now to FIG. 3, an alternative embodiment of the support structure for holding the tube 11 is illustrated. In this embodiment, which can be used in conjunction with a tank 3 that has a cover (not shown) two elongated support members 41, 43, of different lengths are secured in a corner of the tank 3 over the top edge 45 of the tank 3. The elongated support members 41 and 43 each include a U-shaped recess 47, 49, respectively that supports the tube 11 below the top edge 45 of the tank 3. In a preferred embodiment, the elongated support members 41, 43 support the tube 11 in an about horizontal orientation. This arrangement inhibits loss of the feeding medium.

It will be appreciated that the present invention provides a simple, inexpensive system for feeding live insects to fish or other animals living within a tank, such as an aquarium or terrarium. It does not rely upon attracting feral insects that may carry disease from the vicinity of the tank and further does not require human handling of the insects for feeding the animals. In addition, there are no moving parts to maintain, and no outside power is required.

Whereas particular embodiments of the present invention have been described as examples, it will be appreciated that variations of the details may be made without departing from the invention. Therefore, reference should be made to the appended claims rather than to the foregoing discussion of preferred examples, in order to assess the scope of the invention in which exclusive rights are claimed.

I claim:

1. A method of feeding a fish or animal in a tank, comprising the steps of:

providing a container having an opening and a tacky substance surrounding the opening on an outside surface of the container;

providing means for producing a plurality of live flightless insects within the container; and positioning the container with the opening over an open area of the tank.

2. The method of claim 1, wherein the step of providing means for producing a plurality of live flightless insects includes the step of providing a food medium for the live flightless insects to eat.

3. The method of claim 2, wherein the step of providing means for producing a plurality of live flightless insects includes the step of providing a member of the group consisting of a breeding pair of the live flightless insects, a plurality of eggs of the live flightless insects, and a plurality of larvae of the live flightless insects.

4. The method of claim 3, wherein the live flightless insects are members of a flightless variety of Drosophila.

5. A live insect feeder, comprising:

a container including an opening through which a live insect can pass;

a tacky substance surrounding the opening on the outside of the container; and means for feeding live insects within the container.

6. The live insect feeder of claim 5, wherein the means for feeding includes a food medium which the live insect can eat.

7. The live insect feeder of claim 6, wherein the means for feeding includes a support structure for holding the food medium in place within the container.

8. The live insect feeder of claim 6, wherein the container is a tube open at one end.

9. The insect feeder of claim 8, wherein the container includes a removable end cap having a central opening.

10. The live insect feeder of claim 9, wherein the container includes a plug located between the open end and the food medium.

11. The live insect feeder of claim 5, wherein the means for feeding a live insect includes a viable insect selected from the group consisting of an adult flightless winged insect, a larvae of the adult flightless winged insect, and an egg of the adult flightless winged insect.

12. The live insect feeder of claim 11, wherein the viable insect is a flightless variety of Drosophila.

13. A live insect feeder for feeding live insects to a fish or animal living in a tank, comprising:

a container having an opening through which live insects can pass;

a sticky substance located on the outside of the container and surrounding the opening for inhibiting escape of the live insects;

means for feeding the live insects within the container; and means for supporting the container with the opening positioned over the tank.

14. The live insect feeder of claim 13, wherein the container contains a member of the group consisting of a breeding pair of the live insects, a plurality of eggs of the live insects, and a plurality of larvae of the live insects.

15. The live insect feeder of claim 14, wherein the live insects are flightless.

16. The live insect feeder of claim 14, wherein the live insects are a variety of drosophila.

17. The live insect feeder of claim 14, wherein said means for feeding the live insects within the container is an insect feeding medium, and the container includes a removable end cap having a central opening, and a plug located between the insect feeding medium and the end cap.

* * * * *